US008450428B2

(12) United States Patent
Daniel et al.

(10) Patent No.: US 8,450,428 B2
(45) Date of Patent: May 28, 2013

(54) PROCESS FOR PRODUCING WATER-ABSORBENT POLYMER PARTICLES BY POLYMERIZING DROPLETS OF A MONOMER SOLUTION

(75) Inventors: Thomas Daniel, Waldsee (DE); Marco Krüger, Mannheim (DE); Karin Flore, Floersheim-Dalsheim (DE); Stefan Blei, Mannheim (DE); Uwe Stueven, Bad Soden (DE); Norbert Herfert, Altenstadt (DE); Michael A. Mitchell, Waxhaw, NC (US)

(73) Assignee: BASF SE, Ludwigshafen (DE)

( * ) Notice: Subject to any disclaimer, the term of this patent is extended or adjusted under 35 U.S.C. 154(b) by 111 days.

(21) Appl. No.: 13/070,173

(22) Filed: Mar. 23, 2011

(65) Prior Publication Data
US 2011/0237754 A1    Sep. 29, 2011

Related U.S. Application Data

(60) Provisional application No. 61/316,854, filed on Mar. 24, 2010.

(51) Int. Cl.
*C08F 8/00* (2006.01)
*C08F 2/10* (2006.01)
*C08F 20/06* (2006.01)

(52) U.S. Cl.
USPC ....... 525/329.7; 525/53; 525/329.5; 525/384; 525/385; 526/317.1; 526/930

(58) Field of Classification Search
USPC ...... 525/53, 329.5, 329.7, 385, 384; 526/913, 526/930, 317.1
See application file for complete search history.

(56) References Cited

U.S. PATENT DOCUMENTS

| 4,525,527 | A | * | 6/1985 | Takeda et al. ................. 524/831 |
| 5,059,664 | A | * | 10/1991 | Yada et al. .................... 526/240 |
| 5,269,980 | A |   | 12/1993 | Levendis et al. |
| 7,820,873 | B2 | * | 10/2010 | Sun et al. .................... 604/367 |
| 2007/0100115 | A1 |  | 5/2007 | Schmid et al. |
| 2008/0188586 | A1 |  | 8/2008 | Bruhns et al. |
| 2008/0188821 | A1 |  | 8/2008 | Losch et al. |
| 2009/1019203 |    |  | 7/2009 | Stueven et al. |
| 2009/0239071 | A1 |  | 9/2009 | Stueven et al. |
| 2009/0258994 | A1 |  | 10/2009 | Stueven et al. |
| 2009/0315204 | A1 |  | 12/2009 | Losch et al. |
| 2010/0010176 | A1 |  | 1/2010 | Losch et al. |
| 2010/0029866 | A1 |  | 2/2010 | Losch et al. |
| 2010/0068520 | A1 |  | 3/2010 | Stueven |

FOREIGN PATENT DOCUMENTS

| DE | 103 14 466 A1 | 10/2004 |
| DE | 103 40 253 A1 | 3/2005 |
| DE | 10 2004 024 437 A1 | 12/2005 |
| DE | 10 2005 002 412 A1 | 7/2006 |
| EP | 348180 A2 | 12/1989 |
| JP | 01-113406 * | 5/1989 |
| WO | WO-96/40427 A1 | 12/1996 |
| WO | WO-2006/079631 A1 | 8/2006 |
| WO | WO-2008/009580 A1 | 1/2008 |
| WO | WO-2008/009598 A1 | 1/2008 |
| WO | WO-2008/009599 A1 | 1/2008 |
| WO | WO-2008/009612 A1 | 1/2008 |
| WO | WO-2008/040715 A2 | 4/2008 |
| WO | WO-2008/052971 A1 | 5/2008 |
| WO | WO-2008/086976 A1 | 7/2008 |

OTHER PUBLICATIONS

English language Abstract of JP 01-113406; publication date: May 1989.*
Buchholz, Fredric L., et al.. *Modern Superabsorbent Polymer Technology*, "Commercial Processes for the Manufacture of Superabsorbent Polymers," pp. 71-103. New York: John Wiley & Sons, Inc., 1998.

* cited by examiner

*Primary Examiner* — Fred M Teskin
(74) *Attorney, Agent, or Firm* — Marshall, Gerstein & Borun LLP

(57) ABSTRACT

The present invention relates to a process for producing water-absorbent polymer particles by polymerizing droplets of a monomer solution in a surrounding heated gas phase and flowing the gas cocurrent through the polymerization chamber, which comprises thermal postcrosslinking in the presence of steam.

10 Claims, 7 Drawing Sheets

PROCESS FOR PRODUCING WATER-ABSORBENT POLYMER PARTICLES BY POLYMERIZING DROPLETS OF A MONOMER SOLUTION

CROSS-REFERENCE TO RELATED APPLICATIONS

This application claims the benefit of U.S. provisional patent application No. 61/316,854, filed Mar. 24, 2010, incorporated herein by reference in its entirety.

The present invention relates to a process for producing water-absorbent polymer particles by polymerizing droplets of a monomer solution in a surrounding heated gas phase and flowing the gas cocurrent through the polymerization chamber, followed by thermal postcrosslinking in the presence of steam.

The preparation of water-absorbent polymer particles is described in the monograph "Modern Superabsorbent Polymer Technology", F. L. Buchholz and A. T. Graham, Wiley-VCH, 1998, on pages 71 to 103.

Being products which absorb aqueous solutions, water-absorbent polymer particles are used to produce diapers, tampons, sanitary napkins and other hygiene articles, but also as water-retaining agents in market gardening. Water-absorbent polymer particles are also referred to as "superabsorbent polymers" or "superabsorbents".

The preparation of water-absorbent polymer particles by polymerizing droplets of a monomer solution is described, for example, in EP 0 348 180 A1, WO 96/40427 A1, U.S. Pat. No. 5,269,980, DE 103 14 466 A1, DE 103 40 253 A1, DE 10 2004 024 437 A1, DE 10 2005 002 412 A1, DE 10 2006 001 596 A1, WO 2008/009580 A1, WO 2008/009598 A1, WO 2008/009599 A1, WO 2008/009612 A1, WO 2008/040715 A2, WO 2008/052971, and WO 2008/086976 A1.

Polymerization of monomer solution droplets in a gas phase surrounding the droplets ("dropletization polymerization") affords round water-absorbent polymer particles of high mean sphericity (mSPHT). The mean sphericity is a measure of the roundness of the polymer particles and can be determined, for example, with the Camsizer® image analysis system (Retsch Technology GmbH; Haan; Germany). The water-absorbent polymer particles obtained by dropletization polymerization are typically hollow spheres.

It was an object of the present invention to provide water-absorbent polymer particles having improved properties, i.e. comprising water-absorbent polymer particles having a reduced amount of postcrosslinker.

A further object of the present invention was providing a process having low investment costs and low process temperatures.

The object is achieved by a process for producing water-absorbent polymer particles by polymerizing droplets of a monomer solution in a in a surrounding heated gas phase and flowing the gas cocurrent through the polymerization chamber, wherein the temperature of the gas leaving the polymerization chamber is from 90 to 150° C. and the gas velocity inside the polymerization chamber is from 0.1 to 2.5 m/s, followed by thermal postcrosslinking at a temperature of at least 60° C. with postcrosslinkers which comprise groups which can form at least two covalent bonds with the acid groups of the polymer particles in the presence of a gas stream comprising at least 0.01 kg of steam per kg of dry gas.

The present invention is based on the finding that postcrosslinking in the presence of a gas stream having a defined moisture content can reduce the amount of residual postcrosslinker to values below the detection limit.

DETAILED DESCRIPTION OF THE INVENTION

The water-absorbent polymer particles are prepared by polymerizing droplets of a monomer solution comprising
a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a),
e) optionally one or more water-soluble polymers, and
f) water,
in a surrounding heated gas phase and flowing the gas cocurrent through the polymerization chamber, wherein the temperature of the gas leaving the polymerization chamber is from 90 to 150° C. and the gas velocity inside the polymerization chamber is from 0.1 to 2.5 m/s.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropane-sulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Examples for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tatrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for cross-linking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 $g/cm^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-midazolin-2-yl)propane] dihydrochloride and 2,2'-azobis[2-(5-methyl-2-imidazolin-2-yl)propane] dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

The initiators are used in customary amounts, for example in amounts of from 0.001 to 5% by weight, preferably from 0.01 to 2% by weight, based on the monomers a).

Examples of ethylenically unsaturated monomers c) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers d) include polyvinyl alcohol, polyvinylpyrrolidone, starch, starch derivatives, modified cellulose such as methylcellulose or hydroxyethylcellulose, gelatin, polyglycols or polyacrylic acids, polyesters and polyamides, polylactic acid, polyvinylamine, preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pa·s, more preferably from 0.004 to 0.015 Pa·s, most preferably from 0.005 to 0.01 Pa·s. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Polymerization

The monomer solution is metered into the gas phase to form droplets, i.e. using a system described in WO 2008/069639 A1 and WO 2008/086976 A1. The droplets are generated by means of a droplet plate.

A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

Useful coatings include for example fluorous polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization.

It is the poor wettability of the droplet plate that leads to the production of monodisperse droplets of narrow droplet size distribution.

The droplet plate has preferably at least 5, more preferably at least 25, most preferably at least 50 and preferably up to 750, more preferably up to 500 bores, most preferably up to 250. The diameter of the bores is adjusted to the desired droplet size.

The separation of the bores is usually from 10 to 50 mm, preferably from 12 to 40 mm, more preferably from 14 to 35 mm, most preferably from 15 to 30 mm. Smaller separations of the bores cause agglomeration of the polymerizing droplets.

The diameter of the bores is preferably from 50 to 500 µm, more preferably from 100 to 300 µm, most preferably from 150 to 250 µm.

The temperature of the monomer solution as it passes through the bore is preferably from 5 to 80° C., more preferably from 10 to 70° C., most preferably from 30 to 60° C.

A gas flows through the reaction chamber. The carrier gas is conducted through the reaction chamber in cocurrent to the free-falling droplets of the monomer solution, i.e. from the top downward. After one pass, the gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The oxygen content of the carrier gas is preferably from 0.5 to 15% by volume, more preferably from 1 to 10% by volume, most preferably from 2 to 7% by weight.

As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbondioxide, argon, xenon, krypton, neon, helium. Any mixture of carrier gases may be used. The carrier gas may also become loaded with water and/or acrylic acid vapors.

The gas velocity is preferably adjusted such that the flow in the reaction chamber is directed, for example no convection currents opposed to the general flow direction are present, and is from 0.1 to 2.5 m/s, preferably from 0.3 to 1.5 m/s, more preferably from 0.5 to 1.2 m/s, even more preferably from 0.6 to 1.0 m/s, most preferably from 0.7 to 0.9 m/s.

The gas entrance temperature is controlled in such a way that the gas exit temperature, i.e. the temperature with which the gas leaves the reaction chamber, is from 90 to 150° C. or less, preferably from 100 to 140° C., more preferably from 105 to 135° C., even more preferably from 110 to 130° C., most preferably from 115 to 125° C.

The water-absorbent polymer particles can be divided into three categories: water-absorbent polymer particles of Type 1 are particles with one cavity, water-absorbent polymer particles of Type 2 are particles with more than one cavity, and water-absor-bent polymer particles of Type 3 are solid particles with no visible cavity.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having more than one cavity (Type 2) show an improved mechanical stability.

The reaction can be carried out under elevated pressure or under reduced pressure; preference is given to a reduced pressure of up to 100 mbar relative to ambient pressure.

The reaction off-gas, i.e. the gas leaving the reaction chamber, may, for example, be cooled in a heat exchanger. This condenses water and unconverted monomer a). The reaction off-gas can then be reheated at least partly and recycled into the reaction chamber as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal reactor temperature and condensation on the reactor walls is reliably prevented.

Thermal Posttreatment

The residual monomers in the water-absorbent polymer particles obtained by dropletization polymerization are removed by a thermal posttreatment in the presence of a gas stream. The residual monomers can be removed better at relatively high temperatures and relatively long residence times. What is important here is that the water-absorbent polymer particles are not too dry. In the case of excessively dry particles, the residual monomers decrease only insignificantly. Too high a water content increases the caking tendency of the water-absorbent polymer particles. In order that the water-absorbent polymer particles do not dry too rapidly during the thermal posttreatment, the gas flowing in shall already comprise steam.

The thermal posttreatment can be done in an internal and/or an external fluidized bed. An internal fluidized bed means that the product of the dropletization polymerization is accumulated in a fluidized bed at the bottom of the reaction chamber.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.5 to 2.5 m/s, more preferably from 0.6 to 1.5 m/s, most preferably from 0.7 to 1.0 m/s.

In a more preferred embodiment of the present invention the thermal posttreatment is done in an external mixer with moving mixing tools, preferably horizontal mixers, such as screw mixers, disk mixers, screw belt mixers and paddle mixers. Suitable mixers are, for example, Becker shovel mixers (Gebr. Lödige Maschinenbau GmbH; Paderborn; Germany), Nara paddle mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Ruberg continuous flow mixers, Becker shovel mixers and Pflugschar® plowshare mixers are preferred.

The moisture content of the water-absorbent polymer particles during the thermal posttreatment is preferably from 3 to 50% by weight, more preferably from 6 to 30% by weight, most preferably from 8 to 20% by weight.

The temperature of the water-absorbent polymer particles during the thermal posttreatment is preferably from 60 to 140° C., more preferably from 70 to 125° C., very particularly from 80 to 110° C.

The average residence time in the mixer used for the thermal posttreatment is preferably from 10 to 120 minutes, more preferably from 15 to 90 minutes, most preferably from 20 to 60 minutes.

The steam content of the gas is preferably from 0.01 to 1 kg per kg of dry gas, more preferably from 0.05 to 0.5 kg per kg of dry gas, most preferably from 0.1 to 0.25 kg per kg of dry gas.

The thermal posttreatment can be done in a discontinuous external mixer or a continuous external mixer.

The amount of gas to be used in the discontinuous external mixer is preferably from 0.01 to 5 $Nm^3/h$, more preferably from 0.05 to 2 $Nm^3/h$, most preferably from 0.1 to 0.5 $Nm^3/h$, based in each case on kg water-absorbent polymer particles.

The amount of gas to be used in the continuous external mixer is preferably from 0.01 to 5 $Nm^3/h$, more preferably from 0.05 to 2 $Nm^3/h$, most preferably from 0.1 to 0.5 $Nm^3/h$, based in each case on kg/h throughput of water-absorbent polymer particles.

The other constituents of the gas are preferably nitrogen, carbondioxide, argon, xenon, krypton, neon, helium, air or air/nitrogen mixtures, more preferably nitrogen or air/nitrogen mixtures comprising less than 10% by volume of oxygen. Oxygen may cause discoloration.

Postcrosslinking

The polymer particles are postcrosslinked for further improvement of the properties.

Postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230.

Polyvinylamine, polyamidoamines and polyvinylalcohole are examples of multifunctional polymeric postcrosslinkers.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable postcrosslinkers.

Particularly preferred postcrosslinkers are ethylene carbonate, mixtures of propylene glycol, 1,3-propandiole, 1,4-butanediol, mixtures of 1,3-propandiole and 1,4-butanediole, ethylene glycol diglycidyl ether and reaction products of polyamides and epichlorohydrin.

Very particularly preferred postcrosslinkers are 2-hydroxyethyl-2-oxazolidone, 2-oxa-zolidone and 1,3-propanediol.

In addition, it is also possible to use postcrosslinkers which comprise additional polymerizable ethylenically unsaturated groups, as described in DE 37 13 601 A1.

The amount of postcrosslinker is preferably from 0.001 to 2% by weight, more preferably from 0.02 to 1% by weight, most preferably from 0.05 to 0.2% by weight, based in each case on the polymer.

In a preferred embodiment of the present invention, polyvalent cations are applied to the particle surface in addition to the postcrosslinkers before, during or after the postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium, and also mixtures thereof. Possible counterions are chloride, bromide, sulfate, hydrogensulfate, carbonate, hydrogencarbonate, nitrate, hydroxide, phosphate, hydrogenphosphate, dihydrogenphosphate and carboxylate, such as acetate, glycolate, tartrate, formiate, propionate and lactate, and also mixtures thereof. Aluminum sulfate, aluminum acetate, and aluminum lactate are preferred. Apart from metal salts, it is also possible to use polyamines and/or polymeric amines as polyvalent cations. A single metal salt can be used as well as any mixture of the metal salts and/or the polyamines above.

The amount of polyvalent cation used is, for example, from 0.001 to 1.5% by weight, preferably from 0.005 to 1% by weight, more preferably from 0.02 to 0.8% by weight, based in each case on the polymer.

The postcrosslinking is typically performed in such a way that a solution of the postcrosslinker is sprayed onto the hydrogel or the dry polymer particles. After the spraying, the polymer particles coated with the postcrosslinker are dried thermally and cooled, and the postcrosslinking reaction can take place either before or during the drying.

The spraying of a solution of the postcrosslinker is preferably performed in mixers with moving mixing tools, such as screw mixers, disk mixers and paddle mixers. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Ruberg continuous flow mixers and horizontal Pflugschar® plowshare mixers are preferred. The postcrosslinker solution can also be sprayed into a fluidized bed.

If an external mixer or an external fluidized bed is used for thermal posttreatment, the solution of the postcrosslinker can also be sprayed into the external mixer or the external fluidized bed.

The postcrosslinkers are typically used as an aqueous solution. The addition of non-aqueous solvent can be used to adjust the penetration depth of the postcrosslinker into the polymer particles.

The thermal drying is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Nara paddle driers and, in the case of using polyfunctional epoxides, Holo-Flite® dryers are preferred. Moreover, it is also possible to use fluidized bed dryers.

The drying can be effected in the mixer itself, by heating the jacket or blowing in warm air. Equally suitable is a downstream dryer, for example a shelf dryer, a rotary tube oven or a heatable screw. It is particularly advantageous to mix and dry in a fluidized bed dryer.

Preferred drying temperatures are in the range from 50 to 220° C., preferably from 100 to 180° C., more preferably from 120 to 160° C., most preferably from 130 to 150° C. The preferred residence time at this temperature in the reaction mixer or dryer is preferably at least 10 minutes, more preferably at least 20 minutes, most preferably at least 30 minutes, and typically at most 60 minutes.

It is preferable to cool the polymer particles after thermal drying. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures of in the range from 20 to 150° C., preferably from 40 to 120° C., more preferably from 60 to 100° C., most preferably from 70 to 90° C. Cooling using warm water is preferred, especially when contact coolers are used.

Coating

To improve the properties, the water-absorbent polymer particles can be coated and/or optionally moistened. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the postcrosslinked water-absorbent polymer particles. Suitable coatings for controlling the acquisition behavior and improving the permeability (SFC or GBP) are, for example, inorganic inert substances, such as water-insoluble metal salts, organic polymers, cationic polymers and polyvalent metal cations. Suitable coatings for improving the color stability are, for example reducing agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20. Preferred coatings are aluminium monoacetate, aluminium sulfate, aluminium lactate, Brüggolite® FF7 and Span® 20.

Suitable inorganic inert substances are silicates such as montmorillonite, kaolinite and talc, zeolites, activated carbons, polysilicic acids, magnesium carbonate, calcium carbonate, calcium phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the water-absorbent polymer particles are coated with inorganic inert substances, the amount of inorganic inert substances used, based on the water-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoroethylene. Other examples are styrene-isoprene-styrene block-copolymers or styrene-butadiene-styrene block-copolymers.

Suitable cationic polymers are polyalkylenepolyamines, cationic derivatives of polyacrylamides, polyethyleneimines and polyquaternary amines.

Polyquaternary amines are, for example, condensation products of hexamethylenedi-amine, dimethylamine and epichlorohydrin, condensation products of dimethylamine and epichlorohydrin, copolymers of hydroxyethylcellulose and diallyldimethylammo-nium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or poly-functional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the water-absorbent polymer particles are coated with a cationic polymer, the use amount of cationic polymer based on the water-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, nitrate and sulfate. The metal salts are preferably used as a solution or as a stable aqueous colloidal dispersion. The solvents used for the metal salts may be water, alcohols, dimethylfor-mamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the water-absorbent polymer particles are coated with a polyvalent metal cation, the amount of polyvalent metal cation used, based on the water-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophos-phite, salts of sulfinic acids, for example the disodium salt of 2-hydroxy-2-sulfinato-acetic acid, and addition products of aldehydes, for example the disodium salt of 2-hy-droxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

The reducing agents are typically used in the form of a solution in a suitable solvent, preferably water. The reducing agent may be used as a pure substance or any mixture of the above reducing agents may be used.

When the water-absorbent polymer particles are coated with a reducing agent, the amount of reducing agent used, based on the water-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpro-pane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbent polymer particles only insignificantly. The polyols are preferably used as a solution in aqueous or water-miscible solvents.

When the water-absorbent polymer particles are coated with a polyol, the use amount of polyol, based on the water-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Moreover, it is also possible to use a fluidized bed for mixing.

Agglomeration

The water-absorbent polymer particles can further selectively be agglomerated. The agglomeration can take place after the polymerization, the thermal postreatment, the postcrosslinking or the coating.

Useful agglomeration assistants include water and water-miscible organic solvents, such as alcohols, tetrahydrofuran and acetone; water-soluble polymers can be used in addition.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Combination of Thermal Posttreatment, Postcrosslinking and Optionally Coating

In the process according to the present invention the steps of thermal posttreatment and postcrosslinking are combined in one process step. Such combination allows the use of very reactive postcrosslinkers without having any risk of any residual postcrosslinker in the finished product. It also allows the use of low cost equipment and moreover the process can be run at low temperatures which is cost-efficient and avoids discoloration and loss of performance properties of the finished product by thermal degradation.

Postcrosslinkers in this particular preferred embodiment are selected from epoxides, aziridines, polyfuntional epoxides, and polyfunctional aziridines. Examples are ethylene glycol diglycidyl ether, propylene glycol diglycidyl ether, polyethylene glycol diglycidyl ether, polyglycerol polyglycidyl ether, glycerol polyglycidyl ether, sorbitol polyglycidyl ether, pentaerythritol polyglycidyl ether. Such compounds are available for example under the trade name Denacol® (Nagase ChemteX Corporation, Osaka, Japan). These compounds react with the carboxylate groups of the water-absorbent polymers to form crosslinks already at product temperatures of less than 160° C.

The mixer may be selected from any of the equipment options cited in the thermal posttreatment section. Ruberg continuous flow mixers, Becker shovel mixers and Pflugschar® plowshare mixers are preferred.

In this particular preferred embodiment the postcrosslinking solution is sprayed onto the water-absorbent polymer particles under agitation. The temperature of the water-absorbent polymer particles inside the mixer is at least 60° C., preferably at least 80° C., more preferably at least 90° C., most preferably at least 100° C., and preferably not more than 160° C., more preferably not more than 140° C., most preferably not more than 115° C. Thermal posttreatment and postcrosslinking are performed in the presence of a gas stream having a moisture content cited in the thermal posttreatment section.

Following the thermal posttreatment/postcrosslinking the water-absorbent polymer particles are dried to the desired moisture level and for this step any dryer cited in the postcrosslinking section may be selected. However, as only drying needs to be accomplished in this particular preferred embodiment it is possible to use simple and low cost heated contact dryers like a heated screw dryer, for example a Holo-Flite® dryer (Metso Minerals Industries Inc.; Danville; U.S.A.). Alternatively a fluidized bed may be used. In cases where the product needs to be dried with a predetermined and narrow residence time it is possible to use torus disc dryers or paddle dryers, for example a Nara paddle dryer (NARA Machinery Europe; Frechen; Germany), but designed for and operated with low pressure steam or heating liquid as the product temperature during drying does not need to exceed 160° C., preferably does not need to exceed 150° C., more preferably does not need to exceed 140° C., most preferably from 90 to 135° C.

In a preferred embodiment of the present invention, polyvalent cations cited in the post-crosslinking section are applied to the particle surface before, during or after addition of the postcrosslinker by using different addition points along the axis of a horizontal mixer.

In a very particular preferred embodiment of the present invention the steps of thermal post-treatment, postcrosslinking, and coating are combined in one process step. Suitable coatings are cationic polymers, surfactants, and inorganic inert substances that are cited in the coating section. The coating agent can be applied to the particle surface before, during or after addition of the postcrosslinker also by using different addition points along the axis of a horizontal mixer.

The polyvalent cations and/or the cationic polymers can act as additional scavengers for residual postcrosslinkers. In a preferred embodiment of the present invention the postcrosslinkers are added prior to the polyvalent cations and/or the cationic polymers to allow the postcrosslinker to react first.

The surfactants and/or the inorganic inert substances can be used to avoid sticking or caking during this process step under humid atmospheric conditions. A preferred surfactant is Span® 20. Preferred inorganic inert substances are precipitated silicas and fumed silcas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

BRIEF DESCRIPTION OF THE DRAWINGS

Preferred embodiments are depicted in FIGS. 1 to 8.

Figure 3:
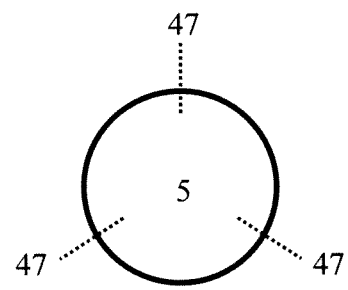
FIG. 3: Arrangement of the T_outlet measurement

The spray dryer outlet temperature is preferably measured at three points around the circumference at the end of the cylindrical part as shown in FIG. 3. The single measurements (47) are used to calculate the average cylindrical spray dryer outlet temperature.

The product accumulated in the internal fluidized bed (27). Conditioned internal fluidized bed gas is fed to the internal fluidized bed (27) via line (25). The relative humidity of the internal fluidized bed gas is preferably controlled by adding steam via line (23).

The spray dryer offgas is filtered in baghouse filter (9) and sent to a condenser column (12) for quenching/cooling. After the baghouse filter (9) a recuperation heat exchanger system for preheating the gas after the condenser column (12) can be used. Excess water is pumped out of the condenser column (12) by controlling the (constant) filling level inside the condenser column (12). The water inside the condenser column (12) is cooled by a heat exchanger (13) and pumped countercurrent to the gas via quench nozzles (11) so that the temperature inside the condenser column (12) is preferably from 20 to 100° C., more preferably from 30 to 80° C., most preferably from 40 to 75° C. The water inside the condenser column (12) is set to an alkaline pH by dosing a neutralizing agent to wash out vapors of monomer a). Aqueous solution from the condenser column (12) can be sent back for preparation of the monomer solution.

The condenser column offgas is split to the drying gas inlet pipe (1) and the conditioned internal fluidized bed gas (25). The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

The product is discharged from the internal fluidized bed (27) via rotary valve (28) into external fluidized bed (29). Conditioned external fluidized bed gas is fed to the external fluidized bed (29) via line (40). The relative humidity of the external fluidized bed gas is preferably controlled by adding steam via line (38). The product holdup in the internal fluidized bed (27) can be controlled via weir height or rotational speed of the rotary valve (28).

The product is discharged from the external fluidized bed (29) via rotary valve (32) into sieve (33). The product holdup in the external fluidized bed (28) can be controlled via weir height or rotational speed of the rotary valve (32). The sieve (33) is used for sieving off overs/lumps.

Figure 1:
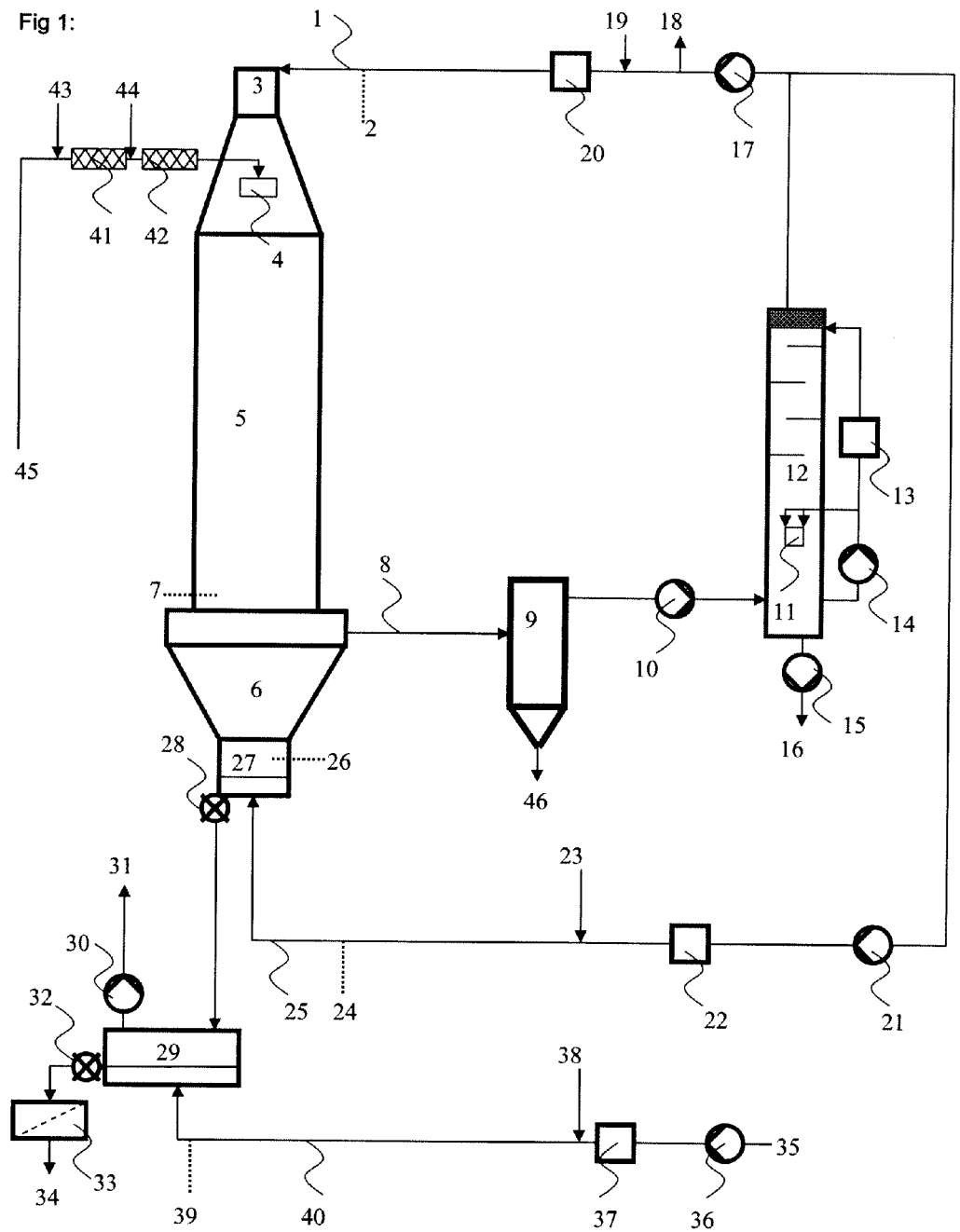
FIG. 1: Process scheme (with external fluidized bed)
Figure 2:
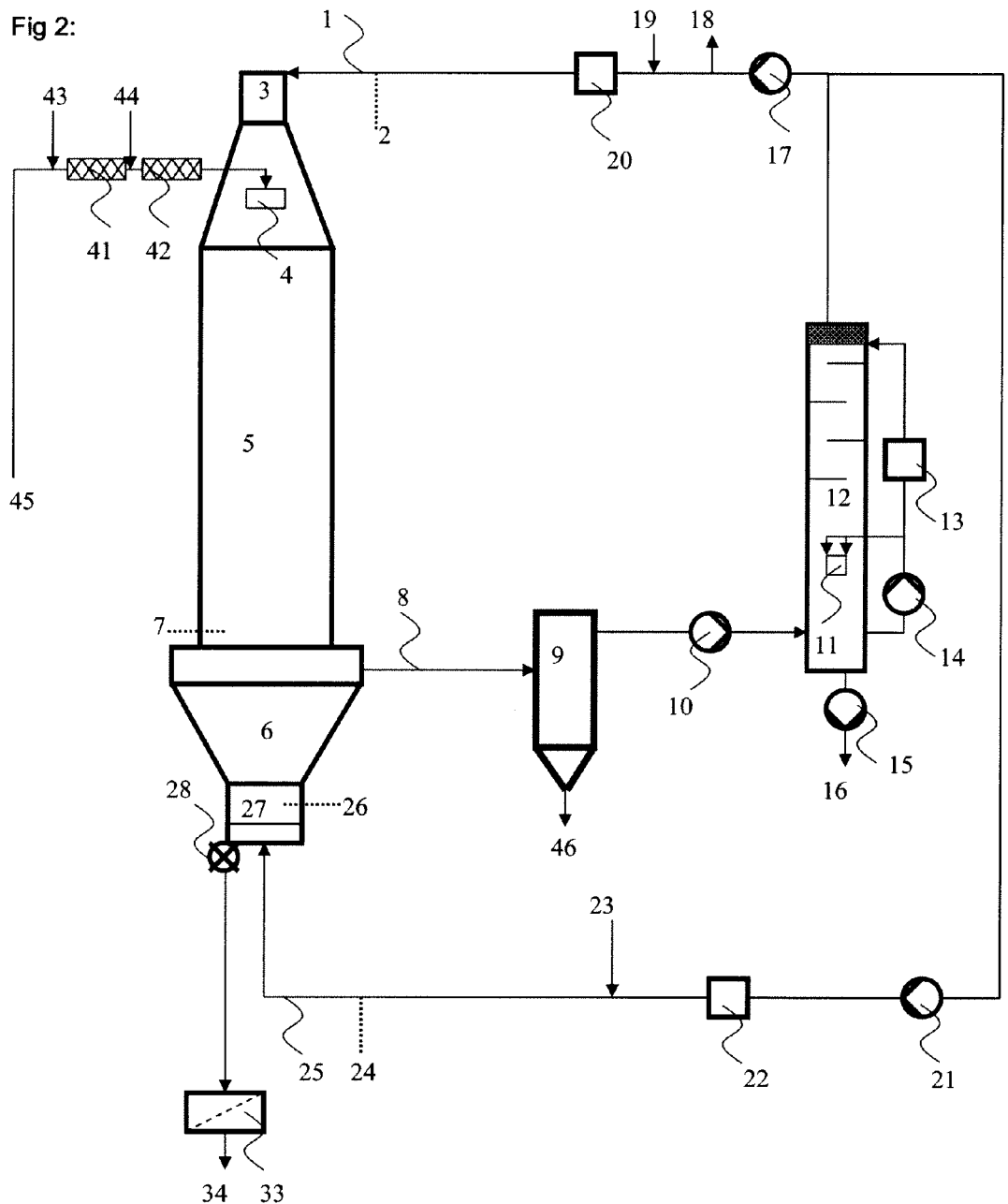
FIG. 2: Process scheme (without external fluidized bed)

The monomer solution is preferably prepared by mixing first monomer a) with a neutralization agent and secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (41) and (42) via lines (43) and (44) as shown in FIG. 1. Preferably a peroxide solution having a temperature of preferably from 5 to 60° C., more preferably from 10 to 50° C., most preferably from 15 to 40° C., is added via line (43) and preferably an azo initiator solution having a temperature of preferably from 2 to 30° C., more preferably from 3 to 15° C., most preferably from 4 to 8° C., is added via line (44). Each initiator is preferably pumped in a loop and dosed via control valves to each dropletizer unit. A second filter unit is preferably used after the static mixer (42). The mean residence time of the monomer solution admixed with the full initiator package in the piping before the droplet plates (57) is preferably less than 60 s, more preferably less than 30 s, most preferably less than 10 s.

Figure 4:
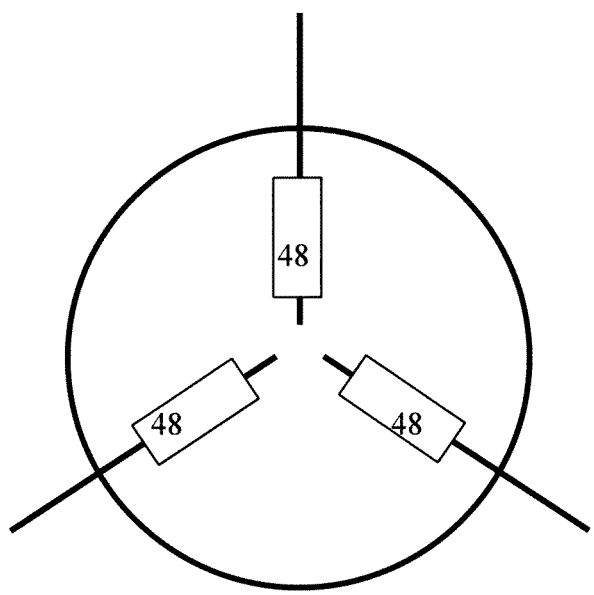
FIG. 4: Arrangement of the dropletizer units

For dosing the monomer solution into the top of the spray dryer preferably three dropletizer units are used as shown in FIG. 4.

Figure 5:
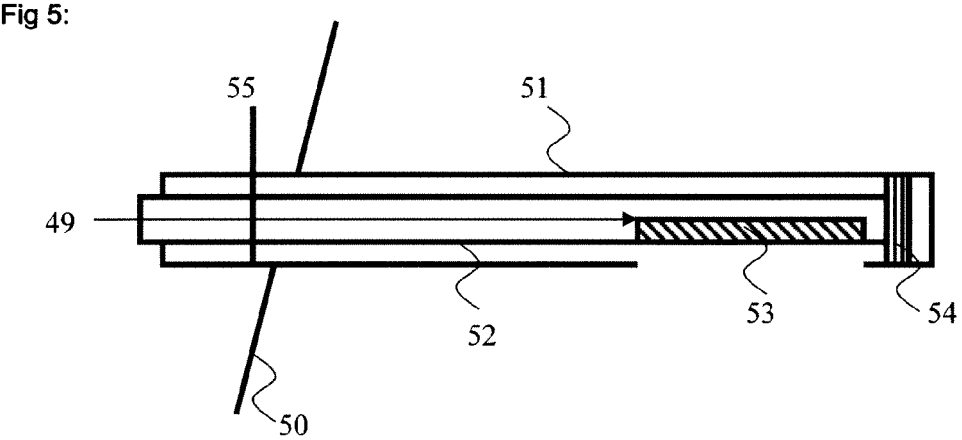
FIG. 5: Dropletizer unit (longitudinal cut)

A dropletizer unit consists of an outer pipe (51) having an opening for the dropletizer cassette (53) as shown in FIG. 5. The dropletizer cassette (53) is connected with an inner pipe (52). The inner pipe (53) having a PTFE block (54) at the end as sealing can be pushed in and out of the outer pipe (51) during operation of the process for maintenance purposes.

Figure 6:
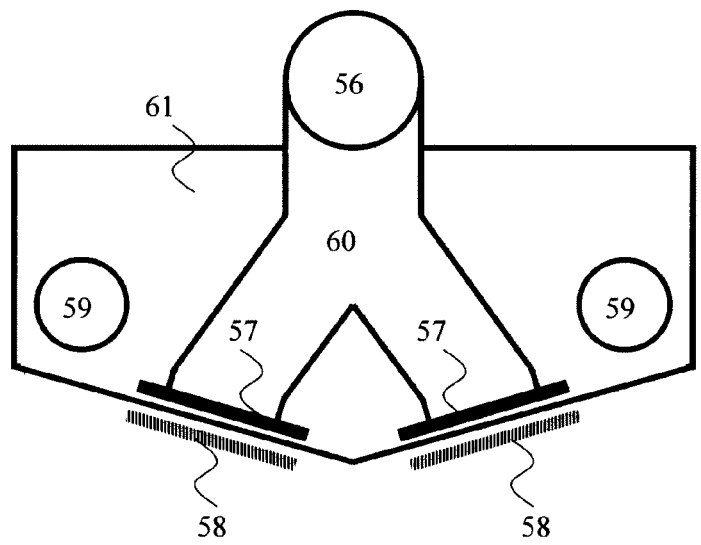
FIG. 6: Dropletizer unit (cross sectional view)
Figure 7:
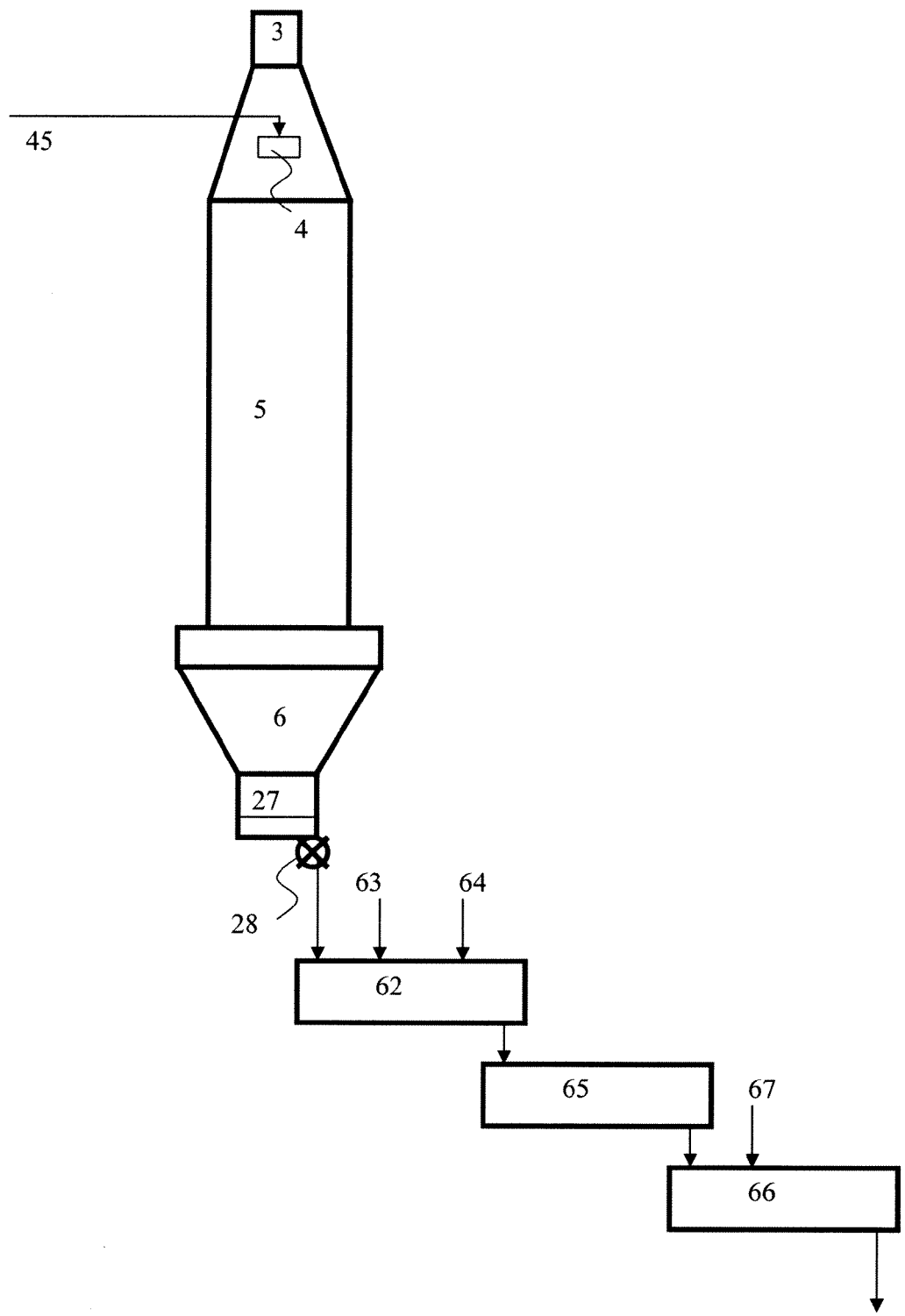
FIG. 7: Process scheme (external thermal posttreatment and postcrosslinking)

The temperature of the dropletizer cassette (61) is controlled to preferably 5 to 80° C., more preferably 10 to 70° C., most preferably 30 to 60° C., by water in flow channels (59) as shown in FIG. 6.

The dropletizer cassette has preferably from 10 to 1500, more preferably from 50 to 1000, most preferably from 100 to 500, bores having a diameter of preferably from 50 to 500 μm, more preferably from 100 to 300 μm, most preferably from 150 to 250 μm. The bores can be of circular, rectangular, triangular or any other shape. Circular bores are preferred. The ratio of bore length to bore diameter is preferably from 0.5 to 10, more preferably from 0.8 to 5, most preferably from 1 to 3. The droplet plate (57) can have a greater thickness than the bore length when using an inlet bore channel. The droplet plate (57) is preferably long and narrow as disclosed in WO 2008/086976 A1. Multiple rows of bores per droplet plate can be used, preferably from 1 to 20 rows, more preferably from 2 to 5 rows.

The dropletizer cassette (61) consists of a flow channel (60) having essential no stagnant volume for homogeneous distribution of the premixed monomer and initiator solutions and two droplet plates (57). The droplet plates (57) have an angled configuration with an angle of preferably from 1 to 90°, more preferably from 3 to 45°, most preferably from 5 to 20°. Each droplet plate (57) is preferably made of stainless steel or fluorous polymers, such as perfluoroalkoxyethylene, polytetrafluoroethylene, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyse the start of polymerization on its surface.

The throughput of monomer including initiator solutions per dropletizer unit is preferably from 150 to 2500 kg/h, more preferably from 200 to 1000 kg/h, most preferably from 300 to 600 kg/h. The throughput per bore is preferably from 0.5 to 10 kg/h, more preferably from 0.8 to 5 kg/h, most preferably from 1 to 3 kg/h.

Water-Absorbent Polymer Particles

The present invention provides water-absorbent polymer particles having more than one cavity wherein the cavities have an inside diameter from preferably 1 to 50 μm, more preferably 2 to 30 μm, even more preferably 5 to 20 μm, most preferably 7 to 15 μm, while the remaining particles have no visible cavities inside. Cavities with less than 1 μm diameter are considered as not visible cavities.

The present invention further provides water-absorbent polymer particles obtainable by the process according to the invention, wherein the polymer particles have a mean sphericity from 0.86 to 0.99, a bulk density of at least 0.58 g/cm$^3$, and a average particle diameter from 250 to 550 μm, and a ratio of particles having one cavity to particles having more than one cavity of less than 1.0.

The water-absorbent polymer particles obtainable by the process according to the invention have a mean sphericity of from 0.86 to 0.99, preferably from 0.87 to 0.97, more preferably from 0.88 to 0.95, most preferably from 0.89 to 0.93. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technolgy GmbH; Haan; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

Water-absorbent polymer particles with relatively low sphericity are obtained by reverse suspension polymerization when the polymer beads are agglomerated during or after the polymerization.

The water-absorbent polymer particles prepared by customary solution polymerization (gel polymerization) are ground and classified after drying to obtain irregular polymer particles. The mean sphericity of these polymer particles is between approx. 0.72 and approx. 0.78.

The inventive water-absorbent polymer particles have a content of hydrophobic solvent of preferably less than 0.005% by weight, more preferably less than 0.002% by weight and most preferably less than 0.001% by weight. The content of hydrophobic solvent can be determined by gas chromatography, for example by means of the headspace technique.

Water-absorbent polymer particles which have been obtained by reverse suspension polymerization still comprise typically approx. 0.01% by weight of the hydrophobic solvent used as the reaction medium.

The inventive water-absorbent polymer particles have a dispersant content of typically less than 1% by weight, preferably less than 0.5% by weight, more preferably less than 0.1% by weight and most preferably less than 0.05% by weight.

Water-absorbent polymer particles which have been obtained by reverse suspension polymerization still comprise typically at least 1% by weight of the dispersant, i.e. ethylcellulose, used to stabilize the suspension.

The water-absorbent polymer particles obtainable by the process according to the invention have a bulk density preferably at least 0.6 g/cm³, more preferably at least 0.65 g/cm³, most preferably at least 0.7 g/cm³, and typically less than 1 g/cm³.

The average particle diameter of the inventive water-absorbent particles is preferably from 320 to 500 μm, more preferably from 370 to 470 μm, most preferably from 400 to 450 μm.

The particle diameter distribution is preferably less than 0.65, more preferably less than 0.62, more preferably less than 0.6.

Particle morphologies of the water-absorbent polymer particles are investigated in the swollen state by microscope analysis. The water-absorbent polymer particles can be divided into three categories: Type 1 are particles with one cavity having diameters typically from 0.4 to 2.5 mm, Type 2 are particles with more than one cavity having diameters typically from 0.001 to 0.3 mm, and Type 3 are solid particles with no visible cavity.

The ratio of particles having one cavity (Type 1) to particles having more than one cavity (Type 2) is preferably less than 0.7, more preferably less than 0.5, most preferably less than 0.4. Lower ratios correlated with higher bulk densities.

The water-absorbent polymer particles obtainable by the process according to the invention have a moisture content of preferably from 0.5 to 15% by weight, more preferably from 3 to 12% by weight, most preferably from 5 to 10% by weight.

In a particular preferred embodiment of the present invention the residual content of unreacted monomer in the water-absorbent polymer particles is reduced by thermal posttreatment with water vapor at elevated temperature. This thermal post-treatment may take place after the water-absorbent polymer particles have left the reaction chamber. The water absorbent particles may also be optionally stored in a buffer silo prior or after thermal post-treatment. Particularly preferred water-absorbent polymer particles have residual monomer contents of not more than 2000 ppm, typically not more than 1000 ppm, preferably less than 700 ppm, more preferably between 0 to 500 ppm, most preferably between 50 to 400 ppm.

The water-absorbent polymer particles obtainable by the process according to the invention have a centrifuge retention capacity (CRC) of typically at least 20 g/g, preferably at least 25 g/g, preferentially at least 28 g/g, more preferably at least 30 g/g, most preferably at least 32 g/g. The centrifuge retention capacity (CRC) of the water-absorbent polymer particles is typically less than 60 g/g.

The water-absorbent polymer particles obtainable by the process according to the invention have an absorbency under a load of 49.2 g/cm² (AUHL) of typically at least 15 g/g, preferably at least 16 g/g, preferentially at least 20 g/g, more preferably at least 23 g/g, most preferably at least 25 g/g, and typically not more than 50 g/g.

The water-absorbent polymer particles obtainable by the process according to the invention have a saline flow conductivity (SFC) of typically at least $10 \times 10^{-7}$ cm³ s/g, usually at least $20 \times 10^{-7}$ cm³ s/g, preferably at least $50 \times 10^{-7}$ cm³ s/g, preferentially at least $80 \times 10^{-7}$ cm³ s/g, more preferably at least $120 \times 10^{-7}$ cm³ s/g, most preferably at least $150 \times 10^{-7}$ cm³ s/g, and typically not more than $300 \times 10^{-7}$ cm³ s/g.

The water-absorbent polymer particles obtainable by the process according to the invention have a free swell gel bed permeability (GBP) of typically at least 5 Darcies, usually at least 10 Darcies, preferably at least 20 Darcies, preferentially at least 30 Darcies, more preferably at least 40 Darcies, most preferably at least 50 Darcies, and typically not more than 250 Darcies.

The inventive water-absorbent polymer particles have an improved mechanical stability and a small particle size distribution. Also, the inventive water-absorbent polymer particles have an improved processibility, a reduced tendency of segregation, a smaller particle size dependent performance deviation, and a reduced dust formation caused by abrasion.

The inventive water-absorbent polymer particles can be mixed with other water-absorbent polymer particles prepared by other processes, i.e. solution polymerization.

The present invention further provides fluid-absorbent articles. The fluid-absorbent articles comprise of (A) an upper liquid-pervious layer
(B) a lower liquid-impervious layer
(C) a fluid-absorbent core between (A) and (B) comprising from 5 to 90% by weight fibrous material and from 10 to 95% by weight water-absorbent polymer particles; preferably from 20 to 80% by weight fibrous material and from 20 to 80% by weight water-absorbent polymer particles; more preferably from 30 to 75% by weight fibrous material and from 25 to 70% by weight water-absorbent polymer particles; most preferably from 40 to 70% by weight fibrous material and from 30 to 60% by weight water-absorbent polymer particles;
(D) an optional acquisition-distribution layer between (A) and (C), comprising from 80 to 100% by weight fibrous material and from 0 to 20% by weight water-absorbent polymer particles; preferably from 85 to 99.9% by weight fibrous material and from 0.01 to 15% by weight water-absorbent polymer particles; more preferably from 90 to 99.5% by weight fibrous material and from 0.5 to 10% by weight water-absorbent polymer particles; most preferably from 95 to 99% by weight fibrous material and from 1 to 5% by weight water-absorbent polymer particles;
(E) an optional tissue layer disposed immediately above and/or below (C); and
(F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapor breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

The water-absorbent polymer particles and the fluid-absorbent articles are tested by means of the test methods described below.

Methods

The measurements should, unless stated otherwise, be carried out at an ambient temperature of 23±2° C. and a relative atmospheric humidity of 50±10%. The water-absorbent polymers are mixed thoroughly before the measurement.

Saline Flow Conductivity (SFC)

Figure 8:
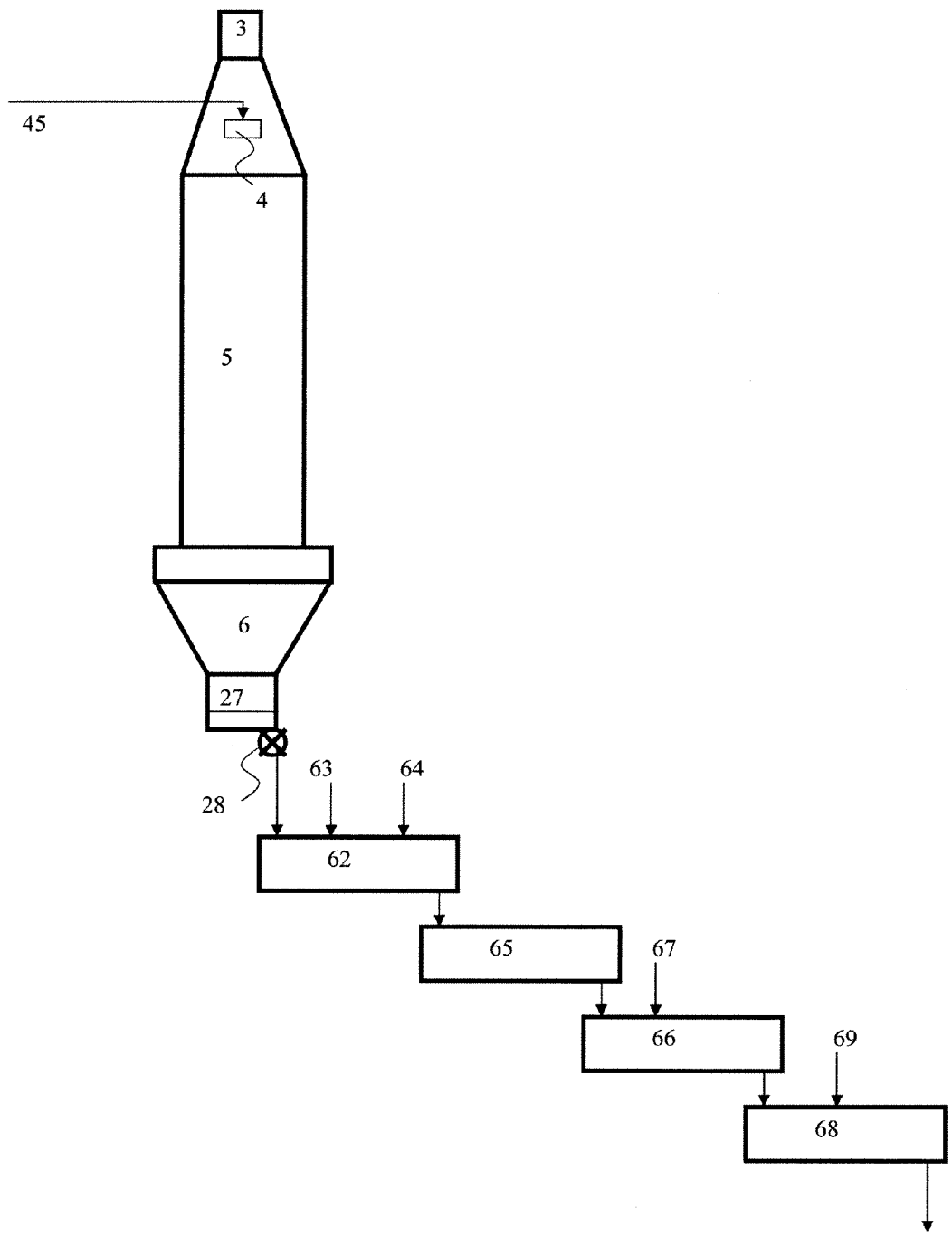
FIG. 8: Process scheme (external thermal posttreatment, postcrosslinking and coating)

The saline flow conductivity is, as described in EP 0 640 330 A1, determined as the gel layer permeability of a swollen gel layer of water-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

$$SFC\ [cm^3\ s/g] = (Fg(t=0) \times L0)/(d \times A \times WP),$$

where $Fg(t=0)$ is the flow rate of NaCl solution in g/s, which is obtained by means of a linear regression analysis of the $Fg(t)$ data of the flow determinations by extrapolation to $t=0$, $L0$ is the thickness of the gel layer in cm, d is the density of the NaCl solution in g/cm$^3$, A is the surface area of the gel layer in cm$^2$ and WP is the hydrostatic pressure over the gel layer in dyn/cm$^2$.

Free Swell Rate (FSR)

1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR\ [g/gs] = W2/(W1 \times t)$$

When the moisture content of the hydrogel-forming polymer is more than 3% by weight, however, the weight W1 must be corrected for this moisture content.

Morphology

Particle morphologies of the water-absorbent polymer particles were investigated in the swollen state by microscope analysis. Approximately 100 mg of the water-absorbent polymer particles were placed on a glass microscope slide. With a syringe, 0.9% aqueous NaCl solution was placed on the water-absorbent polymer particles to swell them. Solution was constantly refilled as it was absorbed by the particles. Care has to be taken that the water-absorbent polymer particles do not run dry. After 30 min swelling time, the slide was put under the microscope (Leica Macroscope Z16 APO, magnification 20×, backlighting by a Schott KL2500 LCD cold light source, camera Leica DFC 420, all by Leica Microsysteme Vertrieb GmbH; Wetzlar; Germany) and 3 pictures were taken at different parts of the sample.

Morphologies can be divided into there categories: Type 1 are particles with one cavity having diameters from 0.4 to 2.5 mm, Type 2 are particles with more than one cavity having diameters from 0.001 to 0.3 mm, and Type 3 are solid particles with no visible cavity.

Figure 9:
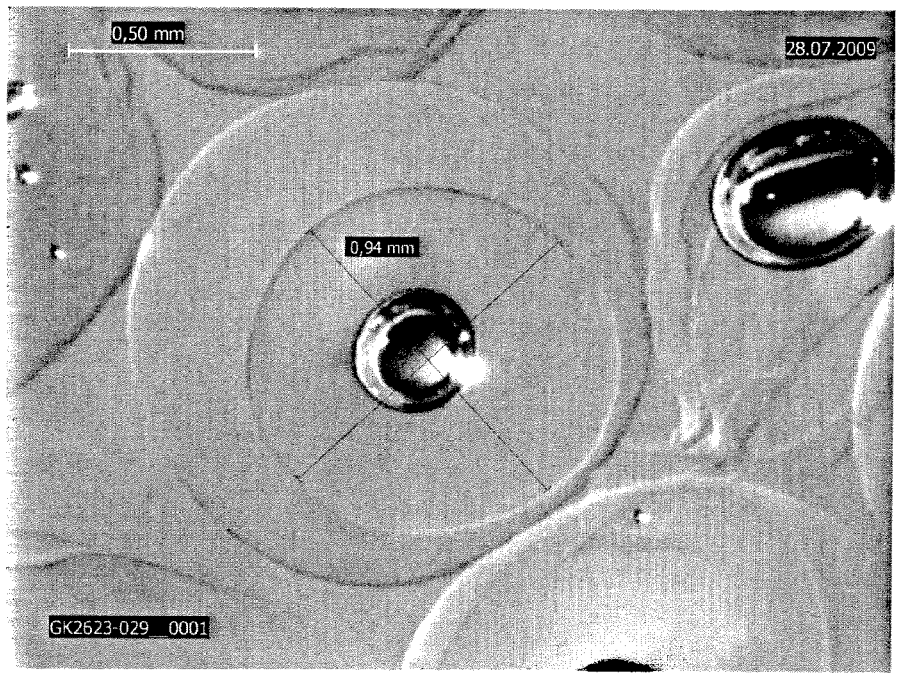
FIG. 9: Swollen state microscope analysis of type 1 polymer particles having a single cavity
Figure 10:
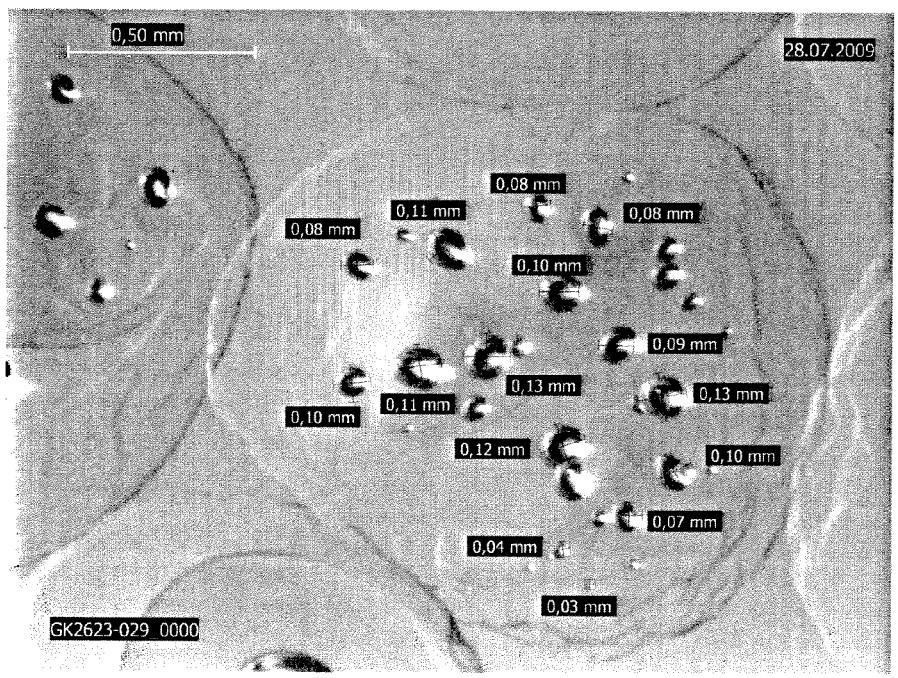
FIG. 10: Swollen state microscope analysis of type 2 polymer particles having a plurality of cavities The reference numerals have the following meanings:
1 Drying gas inlet pipe
2 Drying gas amount measurement
3 Gas distributor
4 Dropletizer units
5 Cocurrent spray dryer, cylindrical part
6 Cone
7 T_outlet measurement
8 Tower offgas pipe
9 Baghouse filter
10 Ventilator
11 Quench nozzles
12 Condenser column, counter current cooling 13 Heat exchanger
14 Pump
15 Pump
16 Water outlet
17 Ventilator
18 Offgas outlet
19 Nitrogen inlet
20 Heat exchanger
21 Ventilator
22 Heat exchanger
23 Steam injection via nozzles
24 Water loading measurement
25 Conditioned internal fluidized bed gas
26 Internal fluidized bed product temperature measurement
27 Internal fluidized bed
28 Product discharge into external fluidized bed, rotary valve
29 External fluidized bed
30 Ventilator
31 External fluidized bed offgas outlet to baghouse filter
32 Rotary valve
33 Sieve
34 End product
35 Filtered air inlet
36 Ventilator
37 Heat exchanger
38 Steam injection via nozzles
39 Water loading measurement
40 Conditioned external fluidized bed gas
41 Static mixer
42 Static mixer
43 Initiator feed
44 Initiator feed
45 Monomer feed
46 Fine particle fraction outlet to rework
47 T_outlet measurement (average temperature out of 3 measurements around tower circumference)
48 Dropletizer unit
49 Monomer premixed with initiator feed
50 Spray dryer tower wall
51 Dropletizer unit outer pipe
52 Dropletizer unit inner pipe
53 Dropletizer cassette
54 Teflon block
55 Valve
56 Monomer premixed with initiator feed inlet pipe connector
57 Droplet plate
58 Counter plate
59 Flow channels for temperature control water
60 Dead volume free flow channel for monomer solution
61 Dropletizer cassette stainless steel block
62 External thermal posttreatment
63 Optional coating feed
64 Postcrosslinker feed
65 Thermal dryer (postcrosslinking)
66 Cooler
67 Optional coating/water feed
68 Coater
69 Coating/water feed The drying gas is feed via a gas distributor (3) at the top of the spray dryer as shown in FIG. 1. The drying gas is partly recycled (drying gas loop) via a baghouse filter (9) and a condenser column (12). The pressure inside the spray dryer is below ambient pressure.

FIG. 9 shows a swollen particle of type 1 with a cavity having a diameter of 0.94 mm and FIG. 10 shows a swollen particle of type 2 with more than 15 cavities having diameters from less than 0.03 to 0.13 mm.

The photograph is analyzed and the numbers of each category is recorded. Undefined or agglomerated particles are omitted from further evaluation. The individual results of the three photographs of each sample are averaged.

Free Swell Gel Bed Permeability (GBP)

The method to determine the free swell gel bed permeability is described in US 2005/0256757, paragraphs [0061] to [0075].

Residual Monomers

The level of residual monomers in the water-absorbent polymer particles is determined by the EDANA recommended test method No. WSP 210.2-05 "Residual Monomers".

Particle Size Distribution

The particle size distribution of the water-absorbent polymer particles is determined with the Camziser® image analysis sytem (Retsch Technology GmbH; Haan; Germany).

For determination of the average particle diameter and the particle diameter distribution the proportions of the particle fractions by volume are plotted in cumulated form and the average particle diameter is determined graphically.

The average particle diameter (APD) here is the value of the mesh size which gives rise to a cumulative 50% by weight.

The particle diameter distribution (PDD) is calculated as follows:

$$PDD = \frac{x_2 - x_1}{APD},$$

wherein $x_1$ is the value of the mesh size which gives rise to a cumulative 90% by weight and $x_2$ is the value of the mesh size which gives rise to a cumulative 10% by weight.

Mean Sphericity

The mean sphericity is determined with the Camziser® image analysis system (Retsch Technology GmbH; Haan; Germany) using the particle diameter fraction from 100 to 1,000 μm.

Moisture Content

The moisture content of the water-absorbent polymer particles is determined by the EDANA recommended test method No. WSP 230.2-05 "Moisture Content".

Centrifuge Retention Capacity (CRC)

The centrifuge retention capacity of the water-absorbent polymer particles is determined by the EDANA recommended test method No. WSP 241.2-05 "Centrifuge Retention Capacity", wherein for higher values of the centrifuge retention capacity lager tea bags have to be used.

Absorbency Under Load (AUL)

The absorbency under high load of the water-absorbent polymer particles is determined by the EDANA recommended test method No. WSP 242.2-05 "Absorption Under Pressure".

Absorbency Under High Load (AUHL)

The absorbency under high load of the water-absorbent polymer particles is determined analogously to the EDANA recommended test method No. WSP 242.2-05 "Absorption Under Pressure", except using a weight of 49.2 g/cm$^2$ instead of a weight of 21.0 g/cm$^2$.

Bulk Density

The bulk density of the water-absorbent polymer particles is determined by the EDANA recommended test method No. WSP 260.2-05 "Density".

Extractables

The level of extractable constituents in the water-absorbent polymer particles is determined by the EDANA recommended test method No. WSP 270.2-05 "Extractables".

The EDANA test methods are obtainable, for example, from the EDANA, Avenue Eugène Plasky 157, B-1030 Brussels, Belgium.

EXAMPLES

Preparation of the Base Polymer

Example 1

The process was performed in a cocurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 2.0 m and a weir height of 0.4 m. The external fluidized bed (EFB) had a length of 3.0 m, a width of 0.65 m and a weir height of 0.5 m.

The drying gas was feed via a gas distributor (3) at the top of the spray dryer. The drying gas was partly recycled (drying gas loop) via a baghouse filter (9) and a condenser column (12). The drying gas was nitrogen that comprises from 1% to 5% by volume of residual oxygen. Before start of polymerization the drying gas loop was filled with nitrogen until the residual oxygen was below 5% by volume. The gas velocity of the drying gas in the cylindrical part of the spray dryer (5) was 0.73 m/s. The pressure inside the spray dryer was 4 mbar below ambient pressure.

The spray dryer outlet temperature was measured at three points around the circumference at the end of the cylindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 125° C. by adjusting the gas inlet temperature via the heat exchanger (20).

The product accumulated in the internal fluidized bed (27) until the weir height was reached. Conditioned internal fluidized bed gas having a temperature of 96° C. and a relative humidity of 45% was fed to the internal fluidized bed (27) via line (25). The relative humidity was controlled by adding steam via line (23). The gas velocity of the internal fluidized bed gas in the internal fluidized bed (27) was 0.8 m/s. The residence time of the product was 35 min.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the cocurrent spray dryer via gas distributor (3). The gas distributor (3) consists of a set of plates providing a pressure drop of 5 to 10 mbar depending on the drying gas amount.

The product was discharged from the internal fluidized bed (27) via rotary valve (28) into external fluidized bed (29). Conditioned external fluidized bed gas having a temperature of 55° C. was fed to the external fluidized bed (29) via line (40). The external fluidized bed gas was air. The gas velocity of the external fluidized bed gas in the external fluidized bed (29) was 0.8 m/s. The residence time of the product was 11 min.

The product was discharged from the external fluidized bed (29) via rotary valve (32) into sieve (33). The sieve (33) was used for sieving off overs/lumps having a particle diameter of more than 850 μm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and 2,2'-azobis[2-(2-imidazolin-2-yl)pro-pane] dihydrochloride solution having a temperature of 5° C. was added via line (44). Each initiator was pumped in a loop and dosed via control valves to each dropletizer unit. A second filter unit having a mesh size of 100 μm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 25° C. by water in flow channels (59) as shown in FIG. 6. The dropletizer cassette had 250 bores having a diameter of 200 μm and a bore separation of 15 mm. The dropletizer cassette (61) consisted of a flow channel (60) having essential no stagnant volume for homogeneous distribution of the premixed monomer and initiator solutions and two droplet plates (57). The droplet plates (57) had an angled configuration with an angle of 10°. Each droplet plate (57) was made of stainless steel and had a length of 500 mm, a width of 25 mm, and a thickness of 1 mm.

The feed to the spray dryer consisted of 10.25% by weight of acrylic acid 32.75% by weigh of sodium acrylate, 0.074% by weight of 3-tuply ethoxylated glycerol triacrylate (approx. 85% strength by weight), 0.12% by weight of 2,2'-azobis[2-(2-imidazolin-2-yl)-propane] dihydrochloride solution (15% by weigh in water), 0.12% by weight of sodium peroxodisulfate solution (15% by weight in water) and water. The degree of neutralization was 71%. The feed per bore was 2.0 kg/h.

The polymer particles exhibit the following features and absorption profile:
CRC of 33.0 g/g
SFC of $12 \times 10^{-7}$ cm$^3$ s/g
AUHL of 24.6 g/g
Moisture content of 6.0 wt. %

The resulting polymer particles had a bulk density of 70.4 g/100 ml, an average particle diameter of 424 μm, a particle diameter distribution of 0.57, and a mean sphericity of 0.91.

Also, the morphology of the resulting polymer particles was analyzed. The ratio of type 1 to type 2 was 0.19.

Example 2

Example 1 was repeated, except that gas velocity of the drying gas in the cylindrical part of the spray dryer (5) was 0.59 m/s and the separation of the bores was 11 mm. For dosing the monomer solution into the top of the spray dryer three dropletizer unit with 267 bores having a diameter of 200 μm were used.

The residence time in the internal fluidized bed was 44 min. The residence time in the internal fluidized bed was 14 min.

The feed to the spray dryer consisted of 10.25% by weight of acrylic acid 32.75% by weigh of sodium acrylate, 0.055% by weight of 3-tuply ethoxylated glycerol triacrylate (approx. 85% strength by weight), 0.12% by weight of 2,2'-azobis[2-(2-imidazolin-2-yl)-propane] dihydrochloride solution (15% by weight in water), 0.12% by weight of sodium peroxodisulfate solution (15% by weight in water) and water. The feed per bore was 1.5 kg/h.

The polymer particles exhibit the following features and absorption profile:

CRC of 35.0 g/g
SFC of $8\times10^{-7}$ $cm^3$ s/g
AUHL of 21.6 g/g
Extractables of 2.1 wt. %
Residual monomers of 616 ppm
Moisture content of 9.4 wt. %
FSR of 0.28 g/gs The resulting polymer particles had a bulk density of 70.7 g/100 ml and an average particle diameter of 426 μm.

Example 3

Example 1 was repeated, except that gas velocity of the drying gas in the cylindrical part of the spray dryer (5) was 0.59 m/s and the separation of the bores was 11 mm. For dosing the monomer solution into the top of the spray dryer three dropletizer unit with 267 bores having a diameter of 200 μm were used.

The conditioned internal fluidized bed gas had a temperature of 98° C. The residence time in the internal fluidized bed was 44 min. The residence time in the internal fluidized bed was 14 min.

The feed to the spray dryer consisted of 10.25% by weight of acrylic acid 32.75% by weigh of sodium acrylate, 0.039% by weight of 3-tuply ethoxylated glycerol triacrylate (approx. 85% strength by weight), 0.12% by weight of 2,2'-azobis[2-(2-imidazolin-2-yl)-propane] dihydrochloride solution (15% by weight in water), 0.12% by weight of sodium peroxodisulfate solution (15% by weight in water) and water. The feed per bore was 1.5 kg/h.

The polymer particles exhibit the following features and absorption profile:

CRC of 40.5 g/g
AUHL of 12.3 g/g
Extractables of 3.9 wt. %
Residual monomers of 818 ppm
Moisture content of 9.0 wt. %

The resulting polymer particles had a bulk density of 67.9 g/100 ml and an average particle diameter of 452 μm.

Postcrosslinking of the Base Polymer

Example 4

800 g of the water-absorbent polymer particles prepared in example 1 were put into a laboratory ploughshare mixer with a heated jacket (model M 5; manufactured by Gebrüder Lödige Maschinenbau GmbH; Paderborn; Germany). A postcrosslinker solution was prepared by mixing 0.80 g of Denacol® EX 512 (polyglycerol polyglycidyl ether; obtained from Nagase ChemteX Corporation; Osaka; Japan), 6 g of propylene glycol, and 12 g of deionized water, into a beaker. At a mixer speed of 450 rpm, the postcrosslinker solution was added dropwise using a syringe to the water-absorbent polymer particles over a three minute time period at room temperature. Five minutes later, 16 g of aluminium lactate solution (25% by weight in water) was added dropwise over a two minute time period. The mixer was then stopped, product sticking to the wall of the mixing vessel was scraped off (and mixed with the bulk), and mixing was continued for 60 minutes at 150 rpm. The batch was heated and held at 140° C. under a gas stream of conditioned nitrogen (20 $Nm^3$/h, 90° C.; 0.24 kg steam per kg dry nitrogen) for 15 minutes. The product was removed from the mixer and allowed to cool in a dessicator. The cooled sample was then sifted, at 150 to 850 μm and characterized as follows:

CRC of 34.3 g/g
SFC of $51\times10^{-7}$ $cm^3$ s/g
AUHL of 27.6 g/g

Residual monomer level was found to be below 500 ppm. No residual postcrosslinker has been detectable.

Example 5

Example 4 was repeated, except that the batch was heated and held at 140° C. under a gas stream of conditioned nitrogen (20 $Nm^3$/h, 90° C.; 0.24 kg steam per kg dry nitrogen) for 45 minutes. The cooled product was then sifted, at 150 to 850 μm and characterized as follows:

CRC of 32.5 g/g
SFC of $65\times10^{-7}$ $cm^3$ s/g
AUHL of 26.9 g/g

Residual monomer level was found to be below 500 ppm. No residual postcrosslinker has been detectable.

Example 6

800 g of the water-absorbent polymer particles prepared in example 2 were put into a laboratory ploughshare mixer with a heated jacket (model M 5; manufactured by Gebrüder Lödige Maschinenbau GmbH; Paderborn; Germany). A postcrosslinker solution was prepared by mixing 0.80 g of Denacol® EX 512 (polyglycerol polyglycidyl ether; obtained from Nagase ChemteX Corporation; Osaka; Japan), 6 g of propylene glycol, and 12 g of deionized water, into a beaker. At a mixer speed of 450 rpm, the postcrosslinker solution was added dropwise using a syringe to the water-absorbent polymer particles over a three minute time period at room temperature. The mixer was then stopped, product sticking to the wall of the mixing vessel was scraped off (and mixed with the bulk), and mixing was continued for 60 minutes at 150 rpm. The batch was heated and held at 140° C. under a gas stream of conditioned nitrogen (20 $Nm^3$/h, 90° C.; 0.24 kg steam per kg dry nitrogen) for 15 minutes. The product was removed from the mixer and allowed to cool in a dessicator. The cooled sample was then sifted, at 150 to 850 μm and characterized as follows:

CRC of 41.0 g/g
AUHL of 30.5 g/g

Residual monomer level was found to be below 500 ppm. No residual postcrosslinker has been detectable.

Example 7

Example 6 was repeated, except that the batch was heated and held at 140° C. under a gas stream of conditioned nitrogen (20 Nm³/h, 90° C.; 0.24 kg steam per kg dry nitrogen) for 45 minutes. The cooled product was then sifted, at 150 to 850 µm and characterized as follows:
CRC of 39.0 g/g
AUHL of 29.2 g/g Residual monomer level was found to be below 500 ppm. No residual postcrosslinker has been detectable.

Example 8

800 g of the water-absorbent polymer particles prepared in example 3 were put into a laboratory ploughshare mixer with a heated jacket (model M 5; manufactured by Gebrüder Lödige Maschinenbau GmbH; Paderborn; Germany). A postcrosslinker solution was prepared by mixing 0.80 g of Denacol EX 512 (polyglycerol polyglycidyl ether; obtained from Nagase ChemteX Corporation; Osaka; Japan), 6 g of propylene glycol, and 12 g of deionized water, into a beaker. At a mixer speed of 450 rpm, the postcrosslinker solution was added dropwise using a syringe to the water-absorbent polymer particles over a three minute time period at room temperature. Five minutes later, 16 g of aluminium lactate solution (25% by weight in water) was added dropwise over a two minute time period. The mixer was then stopped, product sticking to the wall of the mixing vessel was scraped off (and mixed with the bulk), and mixing was continued for 60 minutes at 150 rpm. The batch was heated and held at 115° C. under a gas stream of conditioned nitrogen (20 Nm³/h, 90° C.; 0.24 kg steam per kg dry nitrogen) for 15 minutes. The product was removed from the mixer and allowed to cool in a dessicator. The cooled sample was then sifted, at 150 to 850 µm and characterized as follows:
CRC of 34.7 g/g
SFC of $55 \times 10^{-7}$ cm³ s/g
AUHL of 27.8 g/g Residual monomer level was found to be below 500 ppm. No residual postcrosslinker has been detectable.

The invention claimed is:

1. A process for producing water-absorbent polymer particles by polymerizing droplets of a monomer solution, comprising
   a) at least one ethylenically unsaturated monomer which bears an acid group and may be at least partly neutralized,
   b) at least one crosslinker,
   c) at least one initiator,
   d) optionally one or more ethylenically unsaturated monomer copolymerizable with the monomer mentioned under a), and
   e) water,
in a surrounding heated gas phase and flowing the gas cocurrent through a polymerization chamber, wherein a temperature of the gas leaving the polymerization chamber is from 90 to 125° C. and a gas velocity inside the polymerization chamber is from 0.7 to 2.5 m/s to form the water-absorbent polymer particles, followed by thermal postcrosslinking of the water-absorbent polymer particles at a temperature of at least 60° C. with a postcrosslinker comprising groups which can form two covalent bonds with acid groups of the polymer particles in the presence of a gas stream comprising 0.01 to 1 kg of steam per kg of dry gas.

2. The process according to claim 1, wherein the thermal postcrosslinking is performed in a mixer and the temperature of the water-absorbent polymer particles inside the mixer is not more than 160° C.

3. The process according to claim 2, wherein the thermal postcrosslinking is done in a mixer with moving mixing tools.

4. The process according to claim 1, wherein at least one polyfunctional epoxide is used as postcrosslinker.

5. The process according to claim 1, wherein the temperature of the gas leaving the polymerization chamber is from 115 to 125° C.

6. The process according to claim 1, wherein the gas velocity inside the polymerization chamber is from 0.7 to 0.9 m/s.

7. The process according to claim 1, wherein the thermally postcrosslinked polymer particles are cooled.

8. The process according to claim 1, wherein the monomer a) is acrylic acid to an extent of at least 50 mol %.

9. The process according to claim 1, wherein the monomer a) is neutralized to an extent of at least 25 mol %.

10. The process according to claim 1, wherein the polymer particles have a centrifuge retention capacity of at least 15 g/g.

* * * * *